United States Patent
Skinner et al.

(10) Patent No.: US 10,099,085 B2
(45) Date of Patent: Oct. 16, 2018

(54) TARGETED LIMB REHABILITATION USING A REWARD BIAS

(75) Inventors: Nathaniel E. Skinner, Ann Arbor, MI (US); Arthur D. Kuo, Ypsilanti, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 850 days.

(21) Appl. No.: 13/477,020

(22) Filed: May 21, 2012

(65) Prior Publication Data
US 2013/0137550 A1 May 30, 2013

Related U.S. Application Data

(60) Provisional application No. 61/488,347, filed on May 20, 2011.

(51) Int. Cl.
*A63B 21/005* (2006.01)
*A63B 24/00* (2006.01)
(Continued)

(52) U.S. Cl.
CPC ...... *A63B 24/0087* (2013.01); *A63B 21/4043* (2015.10); *A63B 22/0012* (2013.01); *A63B 22/0056* (2013.01); *A63B 23/03541* (2013.01); *A63B 23/1209* (2013.01); *A63B 24/0059* (2013.01); *A63B 71/0622* (2013.01); *G06F 19/3481* (2013.01); *A63B 21/005* (2013.01);
(Continued)

(58) Field of Classification Search
USPC ........................................................ 482/1, 5
See application file for complete search history.

(56) References Cited

U.S. PATENT DOCUMENTS

2007/0043308 A1* 2/2007 Lee ...................... A61H 1/0237
601/34
2009/0124467 A1* 5/2009 Hildebrandt et al. .......... 482/62
(Continued)

OTHER PUBLICATIONS

Stoloff et al., "Effect of reinforcement history on hand choice in an unconstrained reaching tast", Mar. 23, 2011, Frontiers in Neuroscience, vol. 5, 1-14 (http://journal.frontiersin.org/article/10.3389/fnins.2011.00041/abstract).*
(Continued)

*Primary Examiner* — Andrew S Lo
*Assistant Examiner* — Shila Jalalzadeh Abyan
(74) *Attorney, Agent, or Firm* — Reising Ethington P.C.

(57) ABSTRACT

A multi-limb exercise machine and method that includes a plurality of user-movable input components, an input measurement device associated with each of the input components, a feedback device for providing the user with output information that indicates the difference between a current performance level and a performance target, and a processor that receives input information about user effort applied to each of the input components and communicates the output information to the feedback device. The input components are each configured to be moved by a limb of a user and to resist being moved. The processor determines the difference between performance levels based at least in part on a reward bias that decreases the difference more for effort applied to one of the input components than for effort applied to another of the input components.

16 Claims, 8 Drawing Sheets

(51) Int. Cl.

| | | |
|---|---|---|
| A63B 71/00 | (2006.01) | |
| A63B 71/06 | (2006.01) | |
| A63B 22/00 | (2006.01) | |
| A63B 23/035 | (2006.01) | |
| A63B 23/12 | (2006.01) | |
| G06F 19/00 | (2018.01) | |
| A63B 21/00 | (2006.01) | |
| A63B 21/22 | (2006.01) | |
| A63B 22/06 | (2006.01) | |

(52) U.S. Cl.
CPC ......... *A63B 21/0058* (2013.01); *A63B 21/225* (2013.01); *A63B 21/4035* (2015.10); *A63B 22/0605* (2013.01); *A63B 2022/0038* (2013.01); *A63B 2071/0652* (2013.01); *A63B 2208/0238* (2013.01); *A63B 2220/40* (2013.01); *A63B 2220/51* (2013.01); *A63B 2220/803* (2013.01); *A63B 2220/805* (2013.01); *A63B 2225/20* (2013.01); *A63B 2225/50* (2013.01)

(56) References Cited

U.S. PATENT DOCUMENTS

| | | | |
|---|---|---|---|
| 2010/0075806 A1* | 3/2010 | Montgomery | 482/8 |
| 2011/0071002 A1* | 3/2011 | Gravel et al. | 482/7 |
| 2013/0072353 A1* | 3/2013 | Alessandri et al. | 482/8 |
| 2013/0288858 A1* | 10/2013 | Maresh | A63B 21/0051 482/4 |

OTHER PUBLICATIONS

David J. Reinkensmeyer et al., "Some Key Problems for Robot—Assisted Movement Therapy Research: A Perspective from the University of California at Irvine," Proceedings of the 2007 IEEE 10th International Conference on Rehabilitation Robotics, 2007, pp. 1-7.

L. Lunenburger et al., "Biofeedback in Gait Training with the Robotic Orthosis Lokomat," Proceedings of the 26th Annual International Conference of the IEEE 2004, 26, pp. 1-4.

Helen J. Huang et al., "Neural Coupling Between Upper and Lower Limbs During Recumbent Stepping," Journal of Applied Physiology, 97, 2004, pp. 1-11.

Bruce H. Dobkin, "Motor Rehabilitation After Stroke, Traumatic Brain, and Spinal Cord Injury: Common Denominators Within Recent Clinical Trials," Current Opinion in Neurology, 2009, 22, pp. 1-7.

Joseph Hidler, "Multicenter Randomized Clinical Trial Evaluating the Effectiveness of the Lokomat in Subacute Stroke," Neurorehabilitation and Neural Repair 2009, 23, 5, pp. 1-10.

Hogan N. et al, "Mit-Manus: A Workstation for Manual Therapy and Training I," IEEE International Workshop on Robot and Human Communication, Newman Laboratory for BioMechanics and Human Rehabilitiation, MIT-3-137, Cambridge, MA, 1992, pp. 1-5.

Jordan A. Taylor et al., "Motor Adaptation Scaled by the Difficulty of a Secondary Cognitive Task," PLoS ONE vol. 3, Issue 6, Jun. 2008, pp. 1-11.

Lara A Boyd et al, "Explicit Information Interferes with Implicit Motor Learning of Both Continuous and Discrete Movement Tasks After Stroke," Journal of Neurologic Physical Therapy, vol. 30, No. 2, 2006, pp. 1-12.

Lara A Boyd et al., "Providing Explicit Information Disrupts Implicit Motor Learning After Basal Ganglia Stroke," Learning & Memory 2004, 11, pp. 1-10.

Pauletter M. Van Vleet et al., "Extrinsic Feedback for Motor Learning After Stroke: What is the Evidence?" Disability and Rehabilitation, Jul. 2006, 28(13-14), pp. 1-10.

\* cited by examiner

TARGETED LIMB REHABILITATION USING A REWARD BIAS

CROSS-REFERENCE TO RELATED APPLICATION

This application claims the benefit of U.S. Provisional Application No. 61/488,347, filed May 20, 2011, the entire contents of which are hereby incorporated by reference.

TECHNICAL FIELD

This disclosure relates to techniques for rehabilitating limbs using multi-limb exercise equipment.

BACKGROUND

Rehabilitation is sometimes employed to encourage exercise and strengthen weakened limbs. Persons with hemiparesis or other conditions affecting limb use may chronically prefer to use their unaffected limb or limbs to the point that atrophy and learned disuse of the affected limb or limbs can occur. One of the tasks of physical therapists and strength trainers is to discourage such preferred limb use during traditional resistance training performed on exercise machines. For example, a therapist may give cues and coaching such that a patient uses the affected or weakened limbs during exercise tasks.

One technique that may be used to reduce reliance on the unaffected limb or limbs during therapy is constraint-induced therapy. By having the use of unaffected limbs restricted altogether, the patient has little alternative but to exercise the affected limb. Although sometimes effective, constraint-induced therapy may not be applicable to all types of patients. For example, some stroke patients with poor function may be unable to exercise affected limbs without some assistance, which unaffected limbs could provide. This is especially true for locomotor tasks, in which one leg cannot be substituted for both. In another example, some spinal cord injury patients may have difficulty pedaling an exercise bicycle with the legs alone, but may be able to use assistance from hand pedaling to improve coordination. However, when unaffected limbs are allowed to participate, they may be favored to the exclusion of the affected limb or limbs.

Some more automated approaches have been used to address the assistance problem. For example, one type of device developed to reduce the need for therapist coaching and/or the use of unaffected limbs for assistance is a robotic or other type of automated rehabilitation machine, such as the Lokomat (Hocoma AG, Switzerland), which provides locomotor assistance by moving the patient's legs though a walking motion. Similarly, the MIT Manus robot assists the patient's upper extremity through a reaching motion. However, such automated machines often provide little incentive for the patient to actually use the weakened limb, resulting in less exertion by and strengthening of affected limbs. This lack of participation can greatly limit the effectiveness of assistance robots or similar automated equipment. Vigilance and close supervision provided by a therapist may effectively increase patient effort, but can increase cost and limit therapy times to therapist availability. Patient participation can be elicited by making rehabilitation tasks self-driven. However, as noted above, these types of tasks include the problem of providing a patient incentive to exercise weakened limbs, especially when using only stronger limbs can fulfill the exercise task.

Various techniques have been proposed to address some of these problems. For example, arm guide robots can be programmed to provide assistance only after, and as a reward for, an initial effort by the patient. In another example, some pedaling machines such as certain MOTOmed models (The Reck Company, Betzenweiler, Germany) can provide feedback about the contribution of each side of the body. Additionally, some walking-assist robots can provide the patient with explicit feedback regarding symmetry, limb motion, and effort.

Though some of these approaches may show promise, one problem of some of the feedback systems employed is the complexity of information presented to the patient. Patients may be cognitively taxed by a display of multiple graphs, plots, and/or numerical data that requires interpretation. Such complex feedback can take patient attention away from the task at hand, which is exercising affected limbs.

SUMMARY

In accordance with one aspect of the invention, there is provided a multi-limb exercise machine that includes a plurality of user-movable input components, an input measurement device associated with each of the input components, a feedback device for providing the user with output information that indicates a difference between a current performance level and a performance target, and a processor that receives input information from the input measurement device associated with each of the input components and communicates the output information to the feedback device. The input components are each configured to be moved by a limb of a user and to resist being moved. The input measurement device generates the input information indicating user effort applied to each of the input components, and the processor determines the difference between performance levels based at least in part on a reward bias that decreases the difference more for effort applied to one of the input components than for effort applied to another of the input components.

In accordance with another aspect of the invention, there is provided a method of increasing limb function of a targeted limb of a subject. The method includes the steps of: (a) causing the subject to move an input component using the targeted limb, and to move at least one other input component using another limb for each of the other input components, wherein each input component provides resistance to movement and each input component is moved at least in part by effort exerted by the subject; (b) measuring an amount of effort applied to each input component by the subject; (c) communicating a difference between a composite performance level and a performance target to the subject, the composite performance level including a contribution from each limb; and (d) adjusting the difference according to a reward bias that decreases the difference more for effort exerted by the targeted limb than for effort exerted by the other limb.

In accordance with another aspect of the invention, there is provided a method of increasing limb function of a targeted limb of a subject. The method includes the steps of: (a) measuring individual amounts of effort the subject exerts using the targeted limb and another limb against a common resistance; and (b) rewarding the subject more for a given amount of measured effort exerted by the targeted limb than for the same amount of measured effort exerted by the other limb.

In accordance with yet another aspect of the invention, there is provided a multi-limb exercise machine that includes a pair of user-movable input components configured to resist being moved, wherein one of the pair of input components is configured to be moved by a targeted limb of a user and the other of the pair is configured to be moved by another limb of the user, and a feedback system that provides a user-discernible feedback when the user exerts more for effort by the targeted limb than for effort exerted by the other limb.

BRIEF DESCRIPTION OF THE DRAWINGS

Preferred exemplary embodiments will hereinafter be described in conjunction with the appended drawings, wherein.

DETAILED DESCRIPTION

Figure 1A:
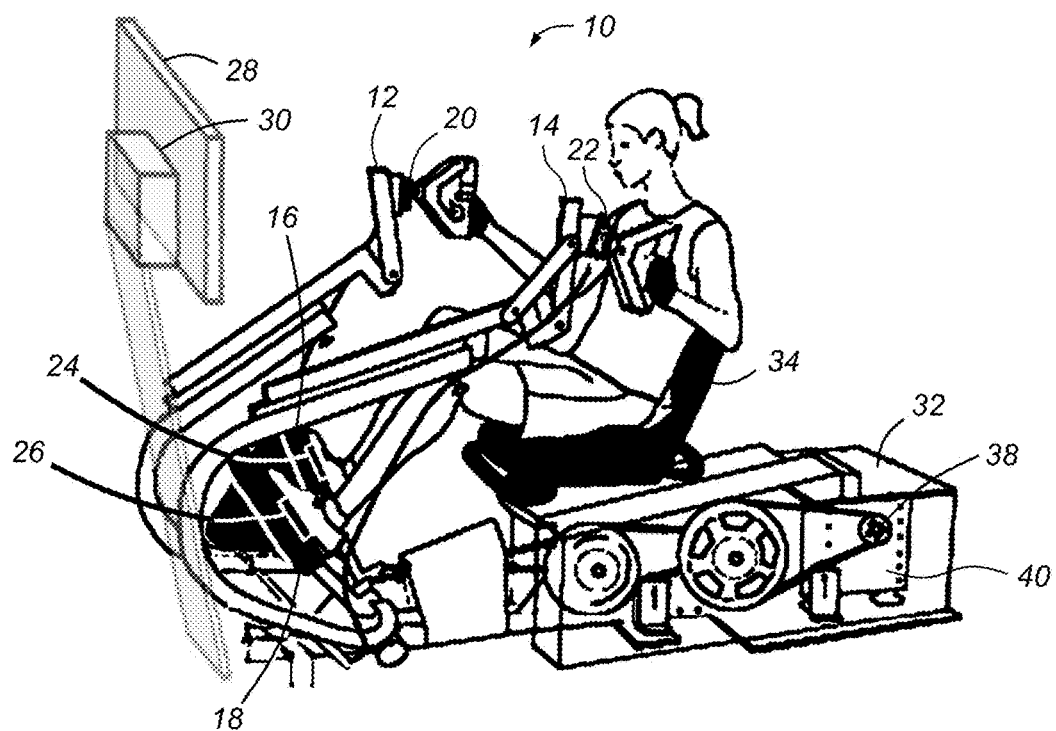
FIG. 1A shows a multi-limb exercise machine, according to one embodiment.

A person's bias in performance toward using one limb set over another to complete a particular exercise task may stem from his or her technique used in achieving the goal feeling the "easiest"—i.e., the person may seek to minimize the overall subjective effort expended to complete the task. This sense of ease can be quantified and used to construct a task with appropriate feedback such that the subjectively "easiest" way to complete the task includes use of the targeted limb or limbs. In other words, an exercise task may be designed to take advantage of a patient's natural tendency to favor an unaffected limb in order to encourage the use of the targeted limb. Additionally, involvement of an affected or otherwise targeted limb can be automatically encouraged without complex feedback displays so that excessive cognitive effort plays a reduced role in physical rehabilitation. The tendencies of people to prefer particular limbs while performing a multi-limb exercise can be quantified and also used to predict the preferred contribution of a particular limb when the task is implicitly biased to favor that limb. Such implicit bias favoring a particular or targeted limb may encourage a subject who requires strengthening or conditioning of the targeted limb to exert more effort with that limb to complete an exercise task than he or she would otherwise exert with the same limb. In other words, a subject may be rewarded for exertion of effort by the targeted limb through an implicit reward bias or a variable weighting of limb power contributions to create an incentive for exercising designated limbs or limb combinations.

Either in conjunction with targeting a specific limb or independently of any such targeting, the embodiments described below may also be used to profile an individual by determining quantitatively what cost is placed by that individual on altering the contribution of different limbs to the combined effort. This subjective cost profile provides an objective, quantifiable measurement of the subjective cost required by the individual to change the effort distribution among limbs, and in some embodiments, may be used in adjusting the reward bias for that individual to more quickly achieve the desired effort level for the targeted limb. As an example, one individual may be relatively responsive to reward biases placed on a particular limb or limbs, having a low subjective cost for changing the effort distribution between limbs. That individual may therefore only need small adjustments in the reward bias to better target a particular limb. Another individual may be somewhat unresponsive to an applied reward bias, and this may be for various reasons such as having a more heavily dominant limb (e.g., heavily right handed) than the average person. In this latter case, a more significant reward bias may be necessary to overcome that subjective cost placed by that individual on redistributing effort from a particular limb or limbs.

These and other concepts are embodied in the methods and apparatus described below in conjunction with the figures. The described methods are useful for increasing the limb function of a targeted limb and may be carried out using the described multi-limb exercise machine that may be configured to perform one or more such methods. Experimental methods and data are additionally disclosed.

Figure 1B:
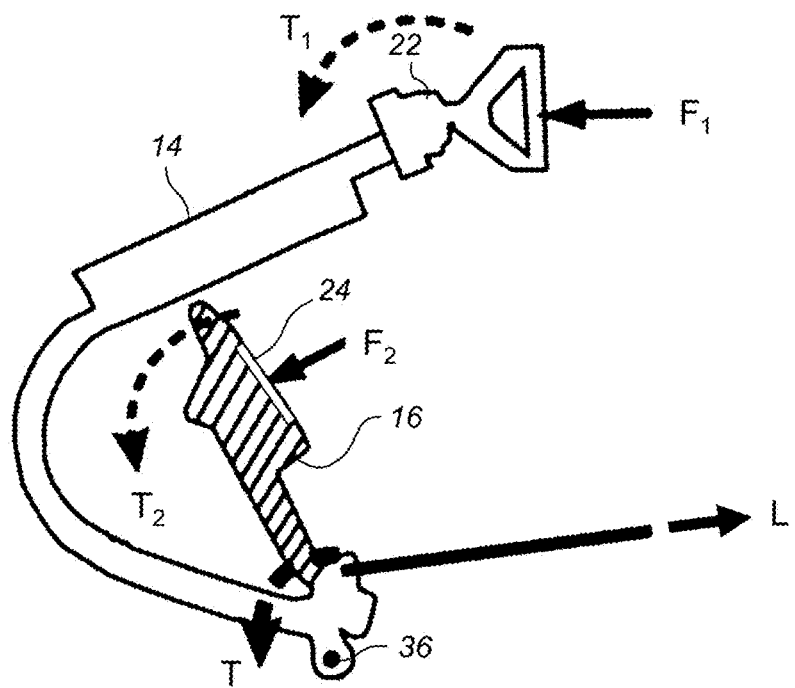
FIG. 1B is a schematic view of two input components of the exercise machine of FIG. 1A, shown coupled together.

Referring to FIGS. 1A and 1B, an illustrative multi-limb exercise machine 10 may be described and generally includes input components 12-18, input measurement devices 20-26, a feedback device 28, and a processor 30. The particular machine 10 shown in FIG. 1A may be referred to as a recumbent stepper machine wherein a user operates the machine in a seated or reclined position as shown. This machine is configured to facilitate coordinated movement among all four limbs of a particular user with the user's right and left legs assuming a stepping motion and the user's left and right arms respectively assuming a simultaneous back and forth motion. Exercise machine 10 may additionally include a variety of other components such as resistance unit 32 and seat 34. Resistance unit 32 can include a series of belts, pulleys, gears, or other components as shown that are configured to provide the input components 12-18 with resistance to movement. In one embodiment, resistance unit 32 includes a magnetic damper placed on an internal flywheel to provide the desired resistance to movement. The level of resistance is preferably adjustable, and various known configurations may be used as the resistance unit. Seat 34 may also be an adjustable component to fit multiple sizes of users.

Input components 12-18 are components that the user, subject, or patient physically interact with to operate the exercise machine. In this embodiment, the input components are user-movable components, and each may be moved by a different limb of the user. More specifically, components 12 and 14 are constructed and arranged to be moved by the right and left arms of the user, respectively. Likewise, components 16 and 18 are constructed and arranged as pedal-like components to be moved by the right and left legs of the user, respectively. In this embodiment, as best shown in FIG. 1B, input components 14 and 16 are paired and rigidly coupled together for simultaneous movement so that the user's left arm and right leg move and/or exert effort together during machine operation. Input components 12 and 18 are paired and rigidly coupled together in the same manner for the user's right arm and left leg. In this particular embodiment, one pair of input components 14, 16 and the other pair of input components 12, 18 are operatively coupled for simultaneous and coordinated movement such that the user exerts effort on each pair of components in an alternating fashion. As shown, a pair of components such as components 14 and 16 may be configured to pivot about a common axis 36 such that, when the input components are moved together in opposition to a resistive load L, forces $F_1$ and $F_2$ applied by the user's arm and leg can each provide a contribution to input component movement. Stated differently, with this type of configuration, the torque T about axis 36 is the sum of $T_1$, generated by the user's arm about axis 36, and $T_2$, generated by the user's leg about the same axis. Components 12 and 18 are configured similarly. Of course, this configuration is non-limiting, as input components 12-18 may be otherwise configured so that, each component may move independently of the others, different individual components may be coupled together, there may be a different number of input components (e.g., for arms or legs only), or the components may move in a sliding, rotating, or other type of motion, for example. It is even possible that the input components are non-movable or that they do not discernibly move during use, such as scale-like components against which a user may simply exert effort but be unable to move, that are configured to have a static load applied thereto and work in conjunction with input measurement devices.

Input measurement devices 20-26 are devices that directly or indirectly measure the effort exerted by the user. In the illustrated embodiment, each input measurement device is a load cell, and each load cell is associated with a different input component so that the effort exerted by the user can be measured as individual contributions from each limb. For example, as shown in FIG. 1B, load cell 22 measures the force $F_1$ applied to input component 14 by the user's left arm, and load cell 24 measures the force $F_2$ applied to input component 16 by the user's right leg. The operation of load cells is well-known, and they may indirectly measure force, torque, and/or movement by providing an output voltage that correlates to the desired measurement and can be interpreted by a processor, such as processor 30, for example. Another type of input measurement device shown in FIG. 1A is an encoder 38. By continuously monitoring or providing information about the relative rotational movement of a resistance-providing motor such as motor 40, for example, the encoder 38 can provide processor 30 with information to help determine real-time positional information about the input components. This type of information may in turn be used to generate information regarding the velocity or acceleration of the input components as well. Other input measurement devices may be included, such as accelerometers, potentiometers, strain gauges, motion detectors, or other known devices. The illustrated location of the measurement devices is arbitrary, and they may be placed in any operable location on the machine. Though each input component may have an input measurement device associated therewith, input components and input measurement devices are not necessarily present in the same number. A single input measurement device may be used with multiple input components. For example, encoder 38 may be used to indirectly determine the velocities of all four input components where processor 30 is provided with sufficient additional information to make such determinations.

Figure 2A:
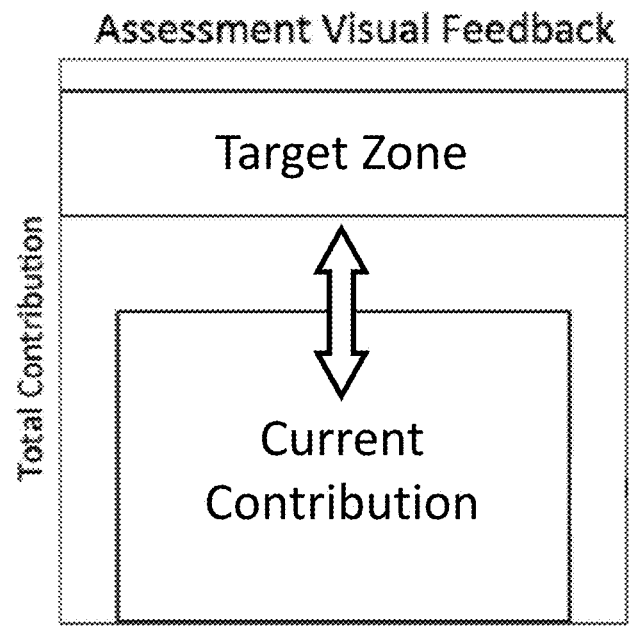
FIGS. 2A-2D are examples of images that may be displayed by a visual feedback device.

Feedback device 28 may be one component of a feedback system that either directly or indirectly rewards the user for effort exerted by the targeted limb or limbs. The reward may be in the form of discernible output information that is adjusted based on particular user efforts, or it may be in the form of one or more other adjustments to the machine that are based on particular user efforts. For instance, feedback device 28 may provide the user with an indication of his or her current or cumulative performance level and its relative proximity to a performance target. In the illustrated embodiment, the feedback device is a visual display that, utilizing information from processor 30 or some other source, can display performance information of various types. FIG. 2A shows one example of an image that can be displayed by a visual feedback device where a performance target is displayed as a colored zone or a line on a bar chart along with the current user performance level so that the proximity of the performance target and performance level relative to one another is shown. In this example, an increase in certain user effort(s) moves the displayed current performance level nearer the displayed performance target. In particular, the visual feedback device 28 in this example can reward the user by disproportionately moving the displayed performance level nearer the performance target based on the amount of effort exerted by a targeted limb or limb group. The magnitude of the disproportionality may be determined at least in part by a reward bias, as discussed in more detail below.

Figure 2B:
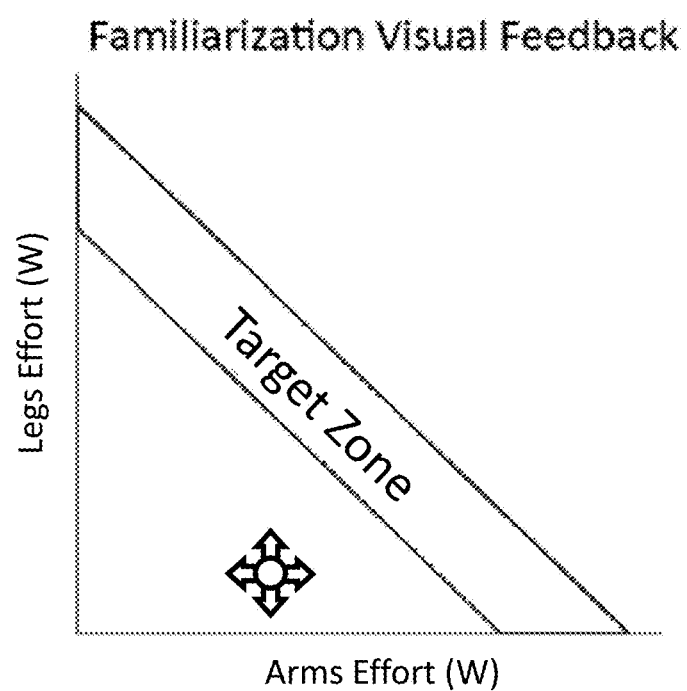
Figure 2C:
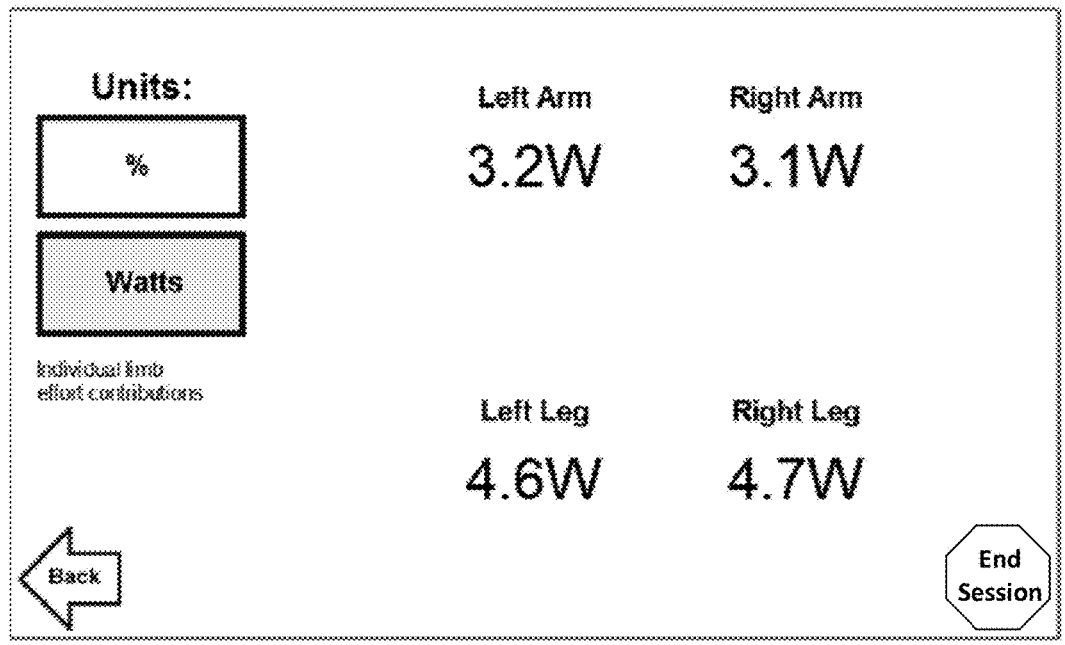
Figure 2D:
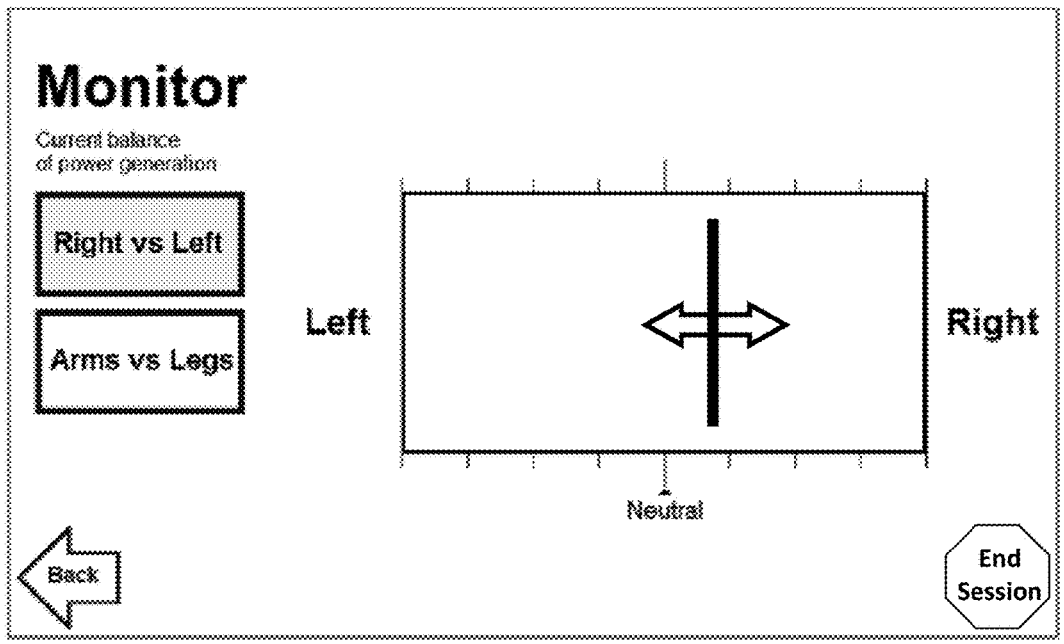

FIG. 2B shows another example of an image that can be displayed by feedback device 28 to provide information about the current user performance and its proximity to the performance target, where the performance of distinct limb groups are shown on the same chart. A visual feedback device may have the capability to display other information as well, besides information designed to reward the user for certain efforts. The effort or performance of individual limbs or limb groups can be displayed by feedback device 28 as shown in FIG. 2C, for example, where the power generated by each limb is included in the displayed image. Other types of information such as performance or effort symmetry between groups of limbs can be displayed by feedback device 28 as shown in FIG. 2D. Feedback device 28 may also or instead provide other types of discernible output information, such as sounds or other auditory cues that change pitch or otherwise noticeably correlate to the relative proximity of the performance target and the current performance level. Any of the user's other senses may be employed by the feedback device as well. For example, the subject's sense of the machine's arm and leg resistance may be employed for feedback, such as by rewarding the use of a targeted limb by lowering the resistance of the overall task or of a particular one or ones of the limb input components. Additionally, feedback device 28 may include its own processor(s) in addition to processor 30 to further process output information received from processor 30 before making the information user-discernible, and it may either be attached to the exercise machine or be a separate unit altogether.

Processor 30 is a component that receives input information from input measurement devices, manipulates or otherwise processes the input information to generate output information, and communicates the output information to the feedback system. It may perform many other functions and receive and communicate information to and from any other component as well. In one embodiment, processor 30 includes a microprocessor that receives the input information in the form of electrical analog or digital signals and communicates the output information to feedback device 28 in similar form. It may itself include a plurality of processors and/or it may be integrated with the feedback system so that it is not a separate component. It may also be located remotely so that it is not physically attached to the machine, for example as a stand-alone laptop computer that receives input information, processes it, and communicates it to the feedback device. Communications to and from the processor may be via electrical, wireless, optical or other connection.

One function of the processor 30 is to provide information to the feedback system regarding the character and/or magnitude of the reward to be provided to the user. The processor may use a reward bias to generate this information. The reward bias may be described as a mathematical function applied to the input information to determine the character and/or magnitude of the user-discernible feedback (reward). In one embodiment, the character of the reward includes lowering the performance target, increasing the performance level, or otherwise communicating to the user that his or her current performance is progressing toward the performance target as a result of greater use of the targeted limb(s). In another embodiment, the character of the reward is physical and can include reducing the resistance of one or more input components to movement so that less effort is required by the user to move it. In this case, the feedback system includes components and/or controls for components that can adjust the resistance in accordance with the information provided by processor 30.

The magnitude of the reward may be proportional to the exerted effort of the targeted limb or limbs, it may have a single magnitude, and in some cases may be a negative reward. The mathematical function can be as simple as a step function that is based on a single threshold effort. For example, an exercise bicycle may be equipped so that the resistance to pedaling can be changed between a high level and low level and so that the resistance is changed from the high level to the low level when the pedal being moved by the targeted limb exerts an amount of effort above a threshold effort. In this example, the pedals are the input components and the feedback system includes components that can change the resistance between high and low levels, such as an actuator that moves a frictional element into or out of contact with a moving component in the system. This relatively simple example rewards the user for use of the targeted limb by reducing the overall effort necessary to operate the machine when the user sufficiently employs the targeted limb. The resistance and threshold levels may be such that the subjective effort of the user is less at the low resistance level than at the high resistance level, even if the actual exerted effort—particularly of the targeted limb—is higher at the low resistance level.

Where user-discernible feedback, such as the visual feedback described above, is provided by the feedback system, processor 30 may determine the relative proximity of the performance target and the current performance level for display by feedback device 28. The performance target may include a desired speed or a power generation threshold, to name a few examples. Either of the displayed performance target or current performance level can be manipulated by processor 30 to reward the user for use of targeted limbs. For example, the performance target may be a threshold minimum speed, where the threshold speed is increased or decreased depending on the input information. For instance, when processor 30 receives input information indicating increased effort or proportion of effort by targeted limbs, it may lower the target speed displayed by feedback device 28. The reward bias may be a function that determines the magnitude and direction of the change in the performance target based on the input information.

The processor 30 may also use a reward bias that includes a mathematical function that transforms the input information to arrive at the composite performance level to be communicated to the user via feedback device 28. This is the type of reward bias used in the examples below. In particular, the function may be applied to the input information from each individual input component, representing applied effort from each of the user's limbs, to arrive at individual contributions from each limb to the composite performance level. In a preferred embodiment, the reward bias weighs the effort exerted by targeted limb(s) more heavily than the efforts exerted from the other limbs when determining the composite performance level communicated to the user by the feedback system. Such mathematical manipulation of the input information to transform it into different output information that includes a bias toward targeted limbs may be particularly useful because it may require fewer additional components or less modification of an existing exercise machine than would be required to provide physical rewards as feedback. However, physical rewards may be used alone or in combination with mathematical manipulation of input information to encourage the user to use targeted limbs.

For the sake of clarity, it is noted that the terms "exerted effort" or "applied effort" are meant to refer to efforts exerted by the user to the input components. "Combined effort" refers to the sum of efforts exerted by individual limbs. The term "contribution" is meant to refer to a particular portion of the composite performance level after the reward bias is applied. The terms "composite performance level" or "current performance level" are meant to refer to an overall performance level associated with the user after the reward bias is applied. By way of example, each limb exerts or applies an individual effort against an input component. Each effort is measured by the associated input measurement device. The total of these individual efforts is the combined effort. The reward bias is applied to each measured effort to arrive at a contribution for each limb. The composite performance level comprises each of the individual limb contributions and does not necessarily represent any particular quantity of actual effort exerted by the user—i.e., the composite performance level may differ from the combined effort.

In one example of the processor applying a simple reward bias, it may be desired that the composite performance level reflect only the effort exerted by the user's legs and that any effort from the user's arms be ignored. The reward bias in this case may be a function that multiplies the measured effort applied by each arm by a factor of zero to determine the individual contribution from each arm. Additionally, the measured effort applied by each leg may be multiplied by a factor of 1 to determine the individual contribution from each leg. These contributions (or adjusted measured efforts) may be summed to arrive at the composite performance level. In another example of the processor applying a reward bias, it may be desired that the composite performance level reflect a true or actual performance level. The reward bias in this case may be a function that multiplies the measured effort applied by each arm and by each leg by a factor of 1 to determine the individual contribution from each limb and summing these contributions to arrive at the composite performance level. In this case, as long as each measured effort is multiplied by the same factor, each limb contribution to the composite performance level is equal, which, for purposes of user feedback regarding proximity to the performance target, sufficiently reflects the applied reward bias.

To cite an example in which the reward bias weighs the efforts exerted by the targeted limb(s) more heavily than the efforts exerted by other limbs when determining the composite performance level, it may be desired to target the legs of a particular user for strengthening or otherwise increasing leg function. In such a case, the reward bias may be a function that multiplies the measured effort applied by each arm by one factor and multiplies the measured effort applied by each leg by a larger factor to determine individual limb contributions to the composite performance level. In this manner, the user is rewarded for more exertion of effort by the legs than by the arms, while not necessarily or completely eliminating the arm input efforts, thereby effectively targeting the legs. In these examples, the factor multipliers are somewhat arbitrary. For instance, in the last example, the leg factor may be 1 and the arm factor may be 0.5 so that the contribution of the leg efforts to the composite performance level is twice that of the arm efforts. But the same effect may be achieved with different proportional factors such as 0.6 and 0.3, respectively. When the composite performance level is communicated to the user, it and/or the target performance level may be normalized or adjusted accordingly by the processor or feedback device to properly indicate their proximity to one another. A single limb, limbs on one side of the body, upper or lower limb sets, or any combination of limbs may be targeted in this fashion by applying a reward bias that sets the contribution of the targeted limb or limbs to the composite performance level at a level higher than their respective measured exerted efforts would otherwise be if the measured exerted efforts were simply summed. Additionally, these examples using simple multipliers for each individual measured effort are only illustrative. A reward bias may use other types of adjustments, such as more complex or non-linear functions, applied to determine individual contribution levels.

As mentioned previously, users of exercise machines may naturally favor a limb other than the targeted one when completing an exercise task, particularly when the targeted limb is weak or experiences pain when exerted and other limbs can instead be used to reach the performance target. This may be the case even with unaffected limbs. For example, the experiments presented below indicate a natural tendency for healthy adults to favor the legs in an exercise task that utilizes all limbs. It is believed that this tendency is based on the user seeking, consciously or not, to minimize his or her own subjective effort when completing an exercise task. That is to say that the user will adjust the effort exerted by the individual limbs in a manner that makes the exercise task "feel" the easiest. In the example experiments presented below, it is shown that manipulating the composite performance level communicated to the user by applying a reward bias to the user's actual exerted efforts is effective to modify the user's technique to include increased exertion of limbs more heavily weighted by the reward bias. While the experiments were conducted with healthy adults as the users or subjects, the results indicate that the concept and application of reward bias is generally an effective method to target particular limbs during multi-limb exercises.

EXAMPLE

An experiment was designed to find the relationship between how limb effort is counted in a work task and the subject's choice for limb use. A recumbent stepper was instrumented to measure effort in the form of power (energy per unit time) from all four of the subject's limbs. The amount that each limb effort counted toward a task goal was then altered via a reward bias, and the resulting individual limb efforts of the subject were measured. This relationship may be used to elicit prescribed levels of effort from limb groups with minimal therapist or robotic intervention or cognitive load.

Ten healthy adults participated in this study. The population included 6 males and 4 females with a mean age of 25 years and standard deviation of 7 years. A commercially available TRS 4000 recumbent stepper (NuStep, Inc., Ann Arbor, Mich.) was selected and instrumented for this experiment because of its current application in self-driven rehabilitation exercises and because its motion is reminiscent of locomotor tasks. Users of the NuStep are seated and alternately push on two pedals with their feet and two handles with their hands to produce cyclic movement. The arms and legs are coupled such that all limbs move in a coordinated fashion, the right arm and left leg moving forward together while the left arm and right leg move backward together, and vice versa.

Force was measured in line with all four limbs, and velocity was measured in the direction of motion to adjudicate subject limb usage for a variety of tasks. Two commercially available load cells (StrainSert, West Conshohocken, Pa.) were placed in line with the hands, and two custom load cells in line with the feet. The custom load cells were designed and manufactured based on resistive force measuring technology by FlexiForce (South Boston, Mass.).

Load, or resistance to motion, was determined experimentally to provide a positive work task (95% positive work), reducing the effects of a negative work task which has inherently different dynamics and energetic costs for the subject. The load was created by back-driving an attached electric motor. The kinematics of the stepper were measured from its geometry and via a rotary encoder attached to the motor. The configuration was used in combination with force data to calculate applied torques and their associated work rates. FIG. 1 includes an illustration of the instrumented stepper.

Force data was collected from the load cells and position data was collected from the optical encoder. The signals were read via a real-time measurement system. A computer screen was used to project visual feedback to the subjects regarding their current performance. The acquisition system sampled at a rate of 100 Hz. The real-time signal processing was handled by RTLab (Opal-RT Montréal, Québec) which runs c-code compiled from Simulink (Matlab, Natick, Mass.).

Figure 3:
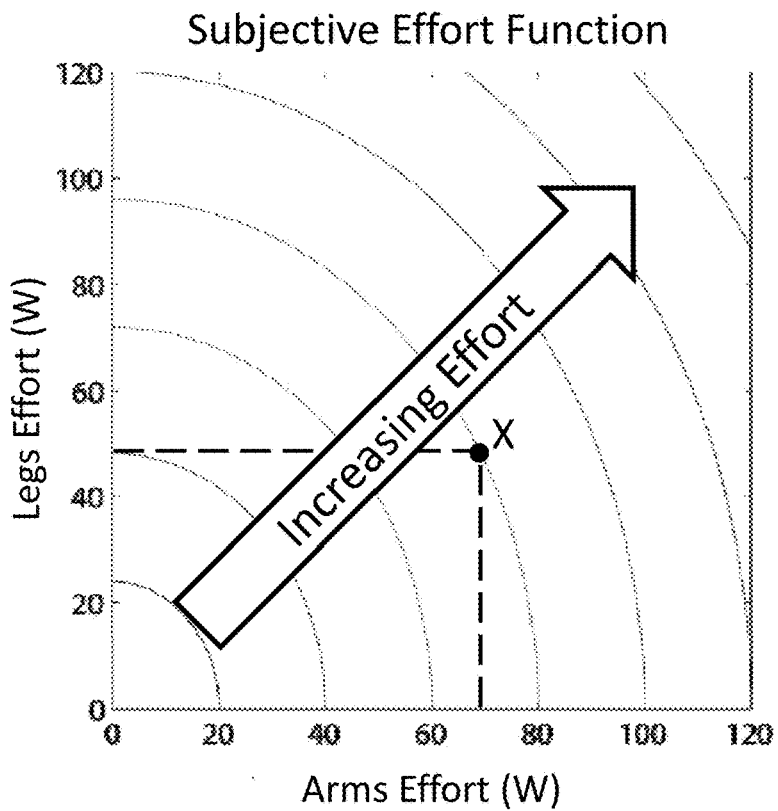
FIG. 3 is a chart showing a subjective effort function, where each curved line represents a constant amount of subjective effort with various combinations of contributions from different limbs.

Users may allocate limb effort to a multi-limb exercise task based on a sense of "subjective effort." Subjective effort may be a quantifiable function of the power generated by the arms and legs, and people may generally seek to minimize their sense of effort while completing the task. FIG. 3 shows a theoretical subjective effort function, represented as a series of curved lines in the chart with increased subjective effort in the direction of the arrow, away from the chart origin. The function may incorporate many aspects of the experience of a task, such as metabolic cost, comfort, habit, etc. While the exact overall shape of the effort function may not be fully known, it is expected to generally increase with greater mechanical power from the limbs. The function is made up of combinations of arms and legs powers that are perceived as equal effort. For example, it may feel equally "easy" to perform 25 W with the arms as it does 30 W with the legs. These two points would have equal values of subjective effort, as would a corresponding set of intermediate combinations of arms and legs along the contour lines in FIG. 3. By way of illustration, point X shown on the chart in FIG. 3 represents a point at which a combined arms effort of about 70 W and legs effort of about 50 W (120 W total effort exerted) feels to the subject like the same overall effort as 80 W using arms alone or 95 W using legs alone—i.e., all three of these arms and legs effort combinations lie along the same contour line of the illustrated subjective effort function.

Exercise tasks were designed to quantify and reveal the unknown subjective function. They were created such that limbs are disproportionately rewarded in their contribution towards a scalar task goal. These disproportionate rewards may be referred to as reward biases, some examples of which are depicted in the form of task constraints (dashed lines) in FIG. 4 at select locations of a subjective effort function chart. For example, if the task constraint only rewards legs it means that no effort from the arms is counted toward the subject's goal or performance target.

Figure 4:
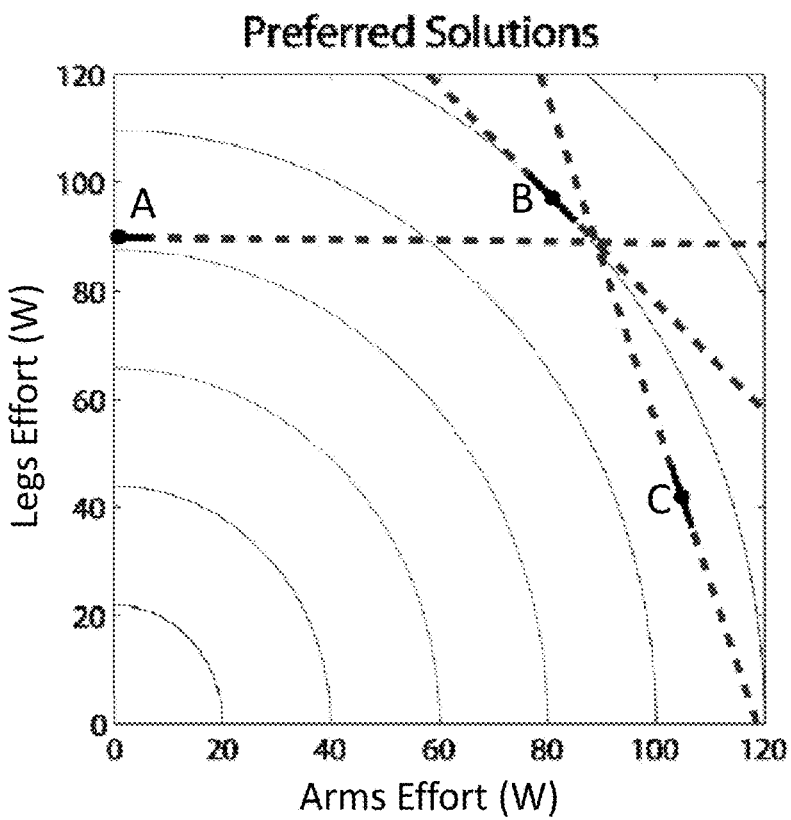
FIG. 4 is a chart showing a subjective effort function with illustrative task constraints depicted as dashed lines and showing points along each task constraint that represent minimized subjective effort.

Assuming that people wish to fulfill the task using the least amount of subjective effort, the chosen solution will be the minimal value in the subjective effort function along the task constraint. Examples of some predicted solutions are shown in FIG. 4 at points A, B, and C where the constraint lines intersect the subjective effort function at minimized values (closest to the origin, which represents zero subjective effort). This approach is analogous to constrained optimization, where the effort function is to be minimized, and the imposed exercise task is a constraint. The optimal solution is thus the intersection of the constraint line with a contour of least effort. Both the subjective effort function and the constraint must have the same slope at the point of minimized subjective effort, so that the entirety of the function can be unveiled by repeating exercises with many different task constraints and performance targets.

In the examples shown in FIG. 4, one task constraint is constructed so that only leg effort is rewarded and no arm effort is rewarded to find point A—i.e., increased effort exerted by the arms only increases the subjective effort required to reach the task goal. In the particular example of point A, the path of least subjective effort is with a leg effort of about 90 W and with no arm effort. Another task constraint is constructed so that arm and leg efforts are equally rewarded to find point B, the path of least subjective effort including a leg effort of about 95 W and an arm effort of about 85 W. For purposes of further familiarization with the subjective effort concept, note that the subjective effort experienced by the user who expends 95 W with leg effort and 85 W with arm effort is the same as if the user had expended only 120 W of arm effort (following the contour line to its intersection with the arm effort axis). But where arms and legs are rewarded equally, it "feels" to the user like the same amount of effort to expend about 180 W of actual combined effort. In other words, including the arms and legs in the task as equal contributors to the task goal makes the task feel easier to the user than using only one set of limbs, even if the user is really expending more overall effort. In the third example for point C, the task constraint is constructed so that arm effort is rewarded more than leg effort. Point C lies at a leg effort of about 40 W and an arm effort of about 110 W. Thus the user would have to exert a small amount of leg effort to minimize his subjective effort. Note that these examples are theoretical to demonstrate the concepts of subjective effort and reward bias and how they may interact with one another.

Figure 5:
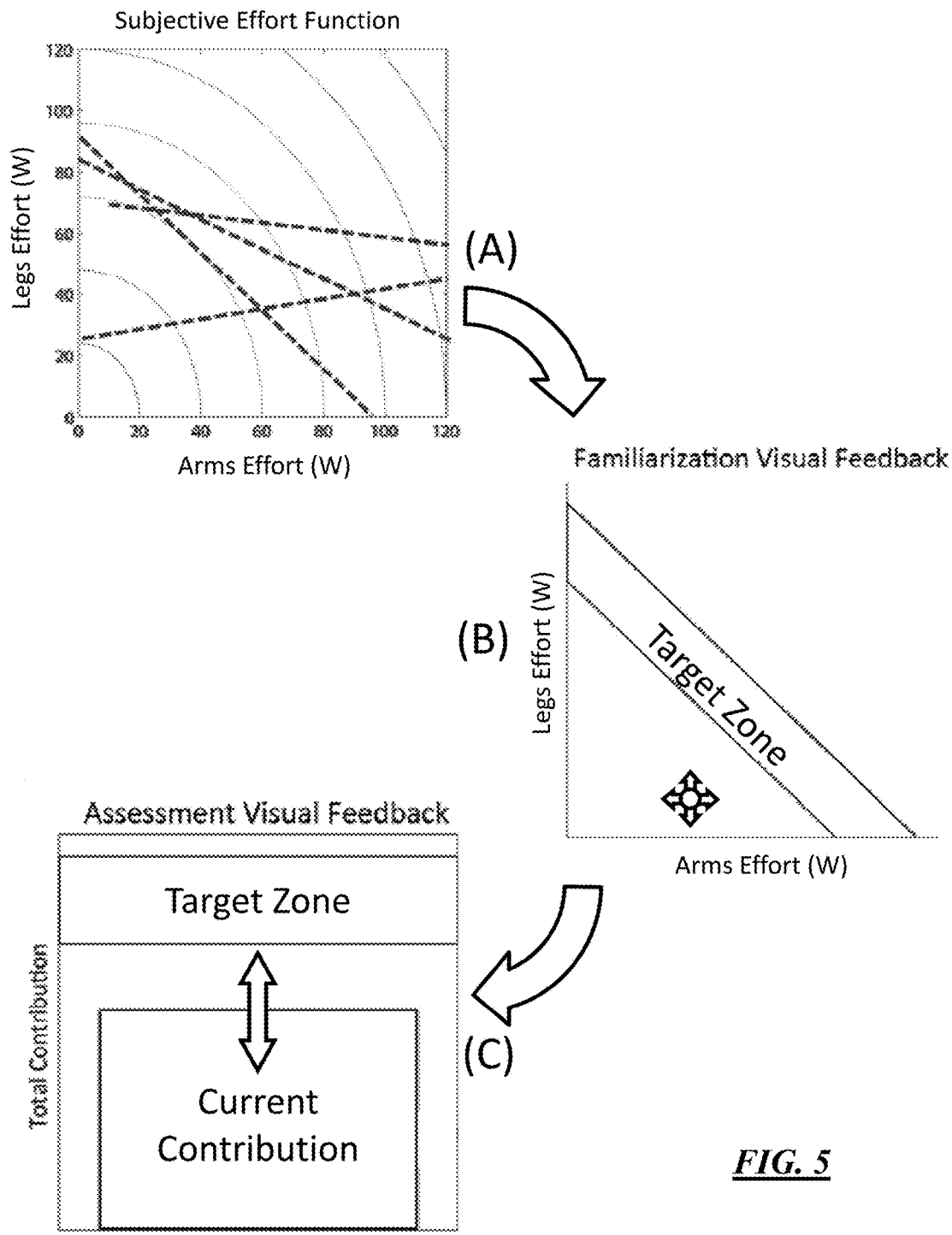
FIG. 5 is a flowchart depicting any of several task constraints (A) being normalized to provide feedback to a user during a familiarization task (B), followed by contributions from different limbs being combined to provide feedback to the user during an assessment task (C)

A protocol was defined for two distinct tasks. The first task familiarized subjects to their subjective feeling of effort along the task constraint. Each subject was presented with visual feedback in which the task constraint, or performance target, was explicitly shown in terms of exerted effort (power) from the arms and legs. A moving average measure of their current performance level in terms of power was indicated with a dot as shown in FIG. 5B. This feedback allowed the subjects to accurately judge if they were satisfying the task constraint and to become familiar with the trade-offs in subjective effort when using one group of limbs more than another.

The task constraints were constructed using the following equation:

$$\text{Task Level} = \frac{(1-\alpha)}{2} * \text{Arms Power} + \frac{(1+\alpha)}{2} * \text{Legs Power} \quad (1)$$

where is the reward bias and ranges from negative one to positive one, effectively rewarding the effort of the arms or legs to various degrees. The "Task Level" is a numerical constant, scaling the overall required power output. The equation takes on the form of a line in the space of arms and legs power for any one trial. The value to use for the task level was experimentally found such that subjects were capable of satisfying the task along the entire line with a neutral reward bias. Successful completion of the task occurred when the subject's current performance level as displayed was within 15% of the task level or performance target, defining the target zone shown in FIG. 5B.

For this particular study, female subjects were given a task level 40% lower than that of male subjects to compensate for strength discrepancies validated within the subject population. The axes for arms and legs contribution were normalized for each trial to eliminate any visual bias stemming from differences in the orientation of the target zone. For example, each of the task constraints from FIG. 5A appeared would have appeared the same (as in FIG. 5B) to the subject when displayed during the familiarization task. Subjects were instructed to maintain contact with the machine with all four limbs at all points in the study, even if they chose not to apply appreciable forces onto the load cells.

After subjects were familiarized with the subjective effort associated with exploring the task constraint, new feedback was displayed in which the limb contributions were summed and shown together as a bar graph with a target zone within 15% of the task level, as shown in FIG. 5C. The subjects were instructed to explore the target zone with different combinations of arms and legs without explicit feedback about individual groups of limbs. Subjects were then asked to choose the combination of limb efforts they most preferred. After becoming familiar with the feedback, two sets of trials were conducted in random order with no repeats within a set. Each subject was able to take a break at any time if fatigued, and a longer break was enforced between the two sets.

In most cases, subjects indicated within 30 to 60 seconds of exploration that they had found a combination of limb efforts that they believed to be most preferable. At this point, data was taken for at least 15 seconds after variation in their distribution of effort subsided and efforts from each limb group appeared constant. The second half of each data set was used to decrease variation further. The work rate produced by each of the limbs was calculated and averaged over the period when the subject was in the target zone. The percent contribution of the legs was calculated and reported as a "performance bias."

The data was analyzed in two forms. In the first, an attempt was made to isolate the effect of altering the reward bias on the subjects' performance bias. In the second, an attempt was made to unveil the shape of the subjects' subjective effort function.

For the first analysis, the proportion of legs effort in relation to total effort was calculated for each trial, and defined to be the performance bias. The relationship between the performance bias and the reward bias was fit to a modified generalized logistic function in the form:

$$\text{Performance Bias} = A + \frac{L - A}{1 + e^{-S*(Reward\ Bias - B)}} \quad (2)$$

A second form of analysis uncovers the subjective effort function itself. Here a set of contours was fitted to the results of all subjects. The contours were fit such that minimizing the subjective effort function subject to the task constraints would result in the manipulation of performance curves found. To model the subjective effort function the equation for a modified cone was used, having the form:

$$\text{Subjective Effort} = \sqrt{(\text{Arms Contribution} - R)^H + \frac{(\text{Legs Contribution} - E)^H}{I}} \quad (3)$$

Figure 6A:
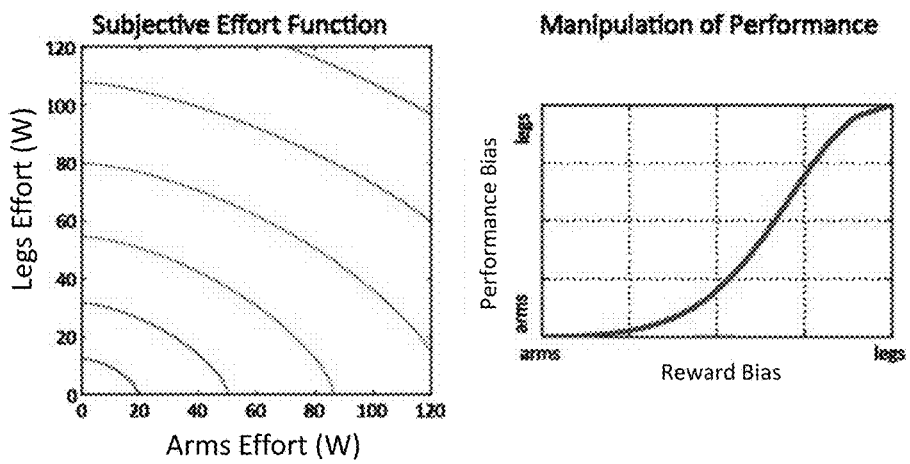
FIGS. 6A-6C each include a chart showing a model subjective effort function and a corresponding chart showing a model of performance bias as a function of reward bias.
Figure 6B:
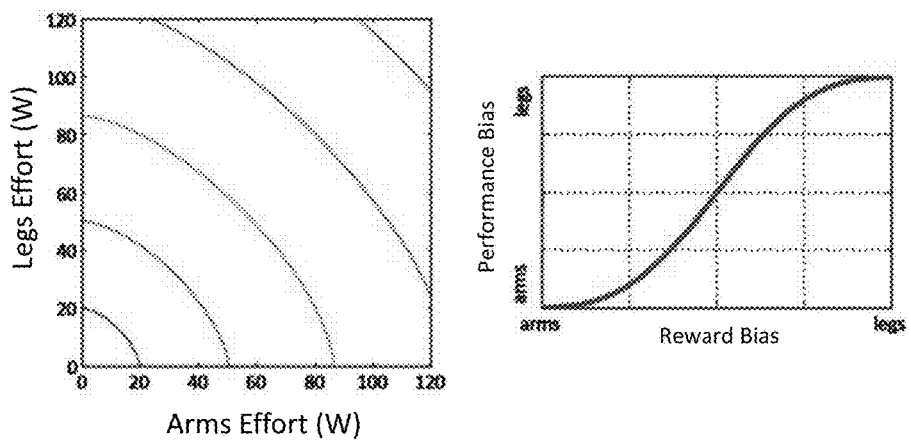
Figure 6C:
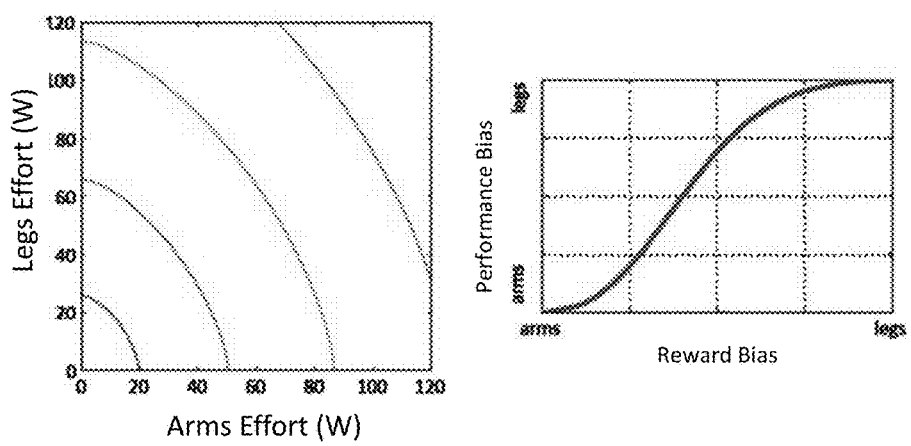

It is believed that the parameters of both fits can be interpreted to have a significant correlate. Moreover, the sets of parameters for both fits are analogous to one another. For example, in both of equations (2) and (3), an inherent bias for greater use of arms or legs is captured by the respective parameters B or I. In the subjective effort function, I represents a scaling of the distance between contours for the legs relative to the arms. In the performance bias vs. reward bias curve, B directly shifts the entire curve left or right, which effectively shifts subject choice for contribution levels more towards legs or arms across biases. Both of these effects are shown in FIGS. 6A-6B, with the variable distance between contour lines in a subjective effort model shown in the left side of each successive figure and the shifting performance bias vs. reward bias model shown in the right side of each successive figure.

A and L in the equation (2) logistic function (performance vs. reward), and R and E in the equation (3) conic function (subjective effort) capture subject unwillingness to forego all effort in either the arms or the legs. In the subjective effort function, they represent the location at which the entire effort function is minimized and, therefore, the minimal amount of effort from the arms and legs that the subject is willing to perform. In the performance bias vs. reward bias function, the A and L represent the lower and upper asymptotes of the curve, again signifying limits on the effort the subject is willing to provide.

Both models also have a similar fourth parameter, parameters S and H, in the manipulation of the performance bias function (2) and the subjective effort function (3), respectively. These parameters determine some aspect of the shape of each function. In the subjective effort function, shape parameter H appears in the exponential of each coordinate of the cone. At H=1, the contour lines of the subject effort function are diagonal lines, each with a slope of −1 such that every point along the contour line represents equal total power provided by arms and legs together. As shape parameter H approaches and reaches a value of 2, the contour lines gradually curve to take on a circular form. Similarly, in the performance bias vs. reward bias curve, shape parameter S varies the curve between a step function and a straight diagonal line. For the step function, if any non-neutral reward bias is given, the subject is compelled to only use the incentivized limb. On the other hand, the straight line example of the performance bias vs. reward bias curve means that the subject's performance is affected proportionately to how much the reward bias is changed.

Figure 7:
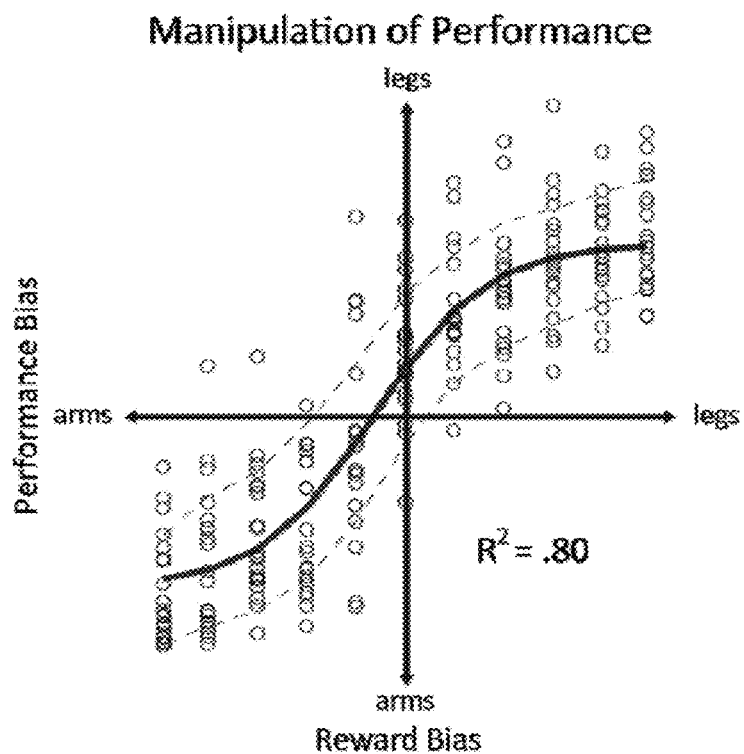
FIG. 7 is a chart showing performance bias as a function of reward bias generated from experimental data fit to the performance bias versus reward bias model used in FIGS. 6A-6C.

Even though subjects in this experiment were unaware of the particular reward bias for each task, they were consistent in their selection of arm and leg efforts selected to satisfy each task. Combining all subjects' changes in performance bias with respect to changes in reward bias and fitting the data to equation (2) above, the best fit curve is shown in FIG. 7, yielding the following parameter values:
A=0.13 (95% CI: 0.07 to 0.19)
L=0.83 (95% CI: 0.78 to 0.87)
B=−0.12 (95% CI: −0.20 to −0.05)
S=4.43 (95% CI: 3.05 to 5.82)
The fit confirms the consistency and repeatability of subject performance ($R^2$=0.80).

A bias exists towards using the legs, as indicated by the performance vs. reward curve. For example, when given a neutral reward bias—i.e., when effort from arms and legs were counted equally—subjects used their legs to produce 57% of the power. There were few cases of subjects using solely the arms or legs. This could be partially accounted for from the stipulation that subjects keep both arms and legs in steady contact with the machine, even if they preferred to perform little or no power with some limbs. In addition, there may be a psychological factor involved. The task is inherently one which calls for effort from all the limbs, and full-body activation seems natural in most cases. Therefore, even if the task is defined such that eliminating the use of either the arms or the legs would lessen the amount of the mechanical power needed to satisfy the goal, the subject may be compelled to use these limbs to preserve the total-body dynamic.

Figure 8:
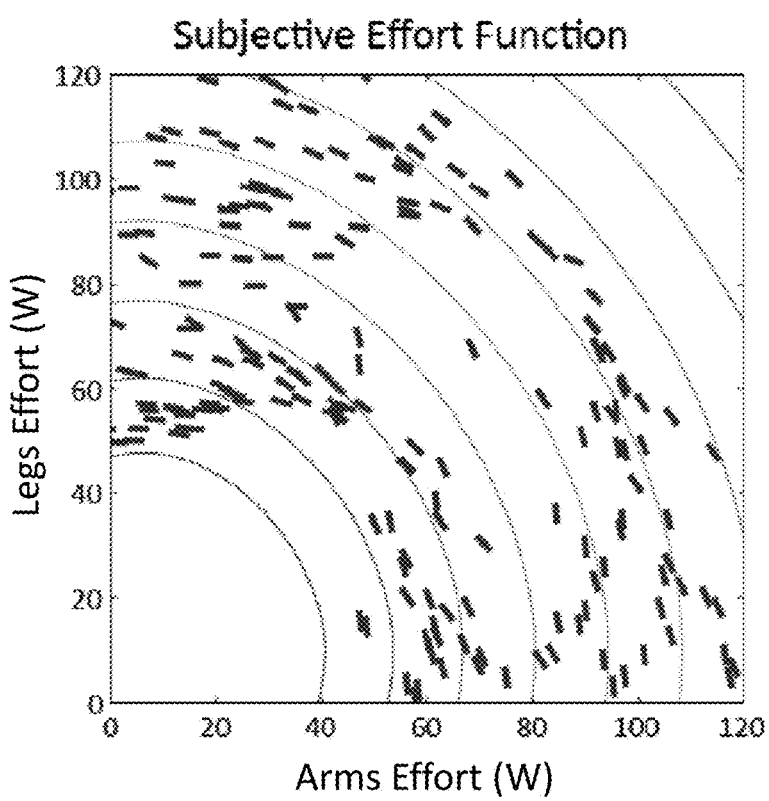
FIG. 8 is a chart showing a subjective effort function generated from experimental data fit to the subjective effort model used in FIGS. 6A-6C.

Contours of equal subjective effort were deduced base on equation (3). The best fit series of curves is shown in FIG. 8, yielding the following parameter values:
R=6.30 (95% CI: 3.98 to 8.61)
E=9.88 (95% CI: 6.20 to 13.57)
I=1.10 (95% CI: 0.79 to 1.4)
H=1.80 (95% CI: 1.52 to 2.08).

In general, the data suggests that the effort function increases with greater power from the arms and legs. This is intuitively correct, as one would expect that subjective effort would scale relatively well with mechanical power output. Furthermore, it is noted that boundary conditions at each set of axes are consistent with the predictions. For example, where each of the contour lines intersect and axis the contours are nearly perpendicular to the axis, such that fastest descent of the effort function is towards the origin. It is noted that these boundary conditions were not enforced by definition from the equation (3) model. There are degrees of freedom, in the form of parameters A and L, to translate the entire set of contours anywhere in the plane to provide boundary conditions at the axes of any arbitrary slope.

Figure 9:
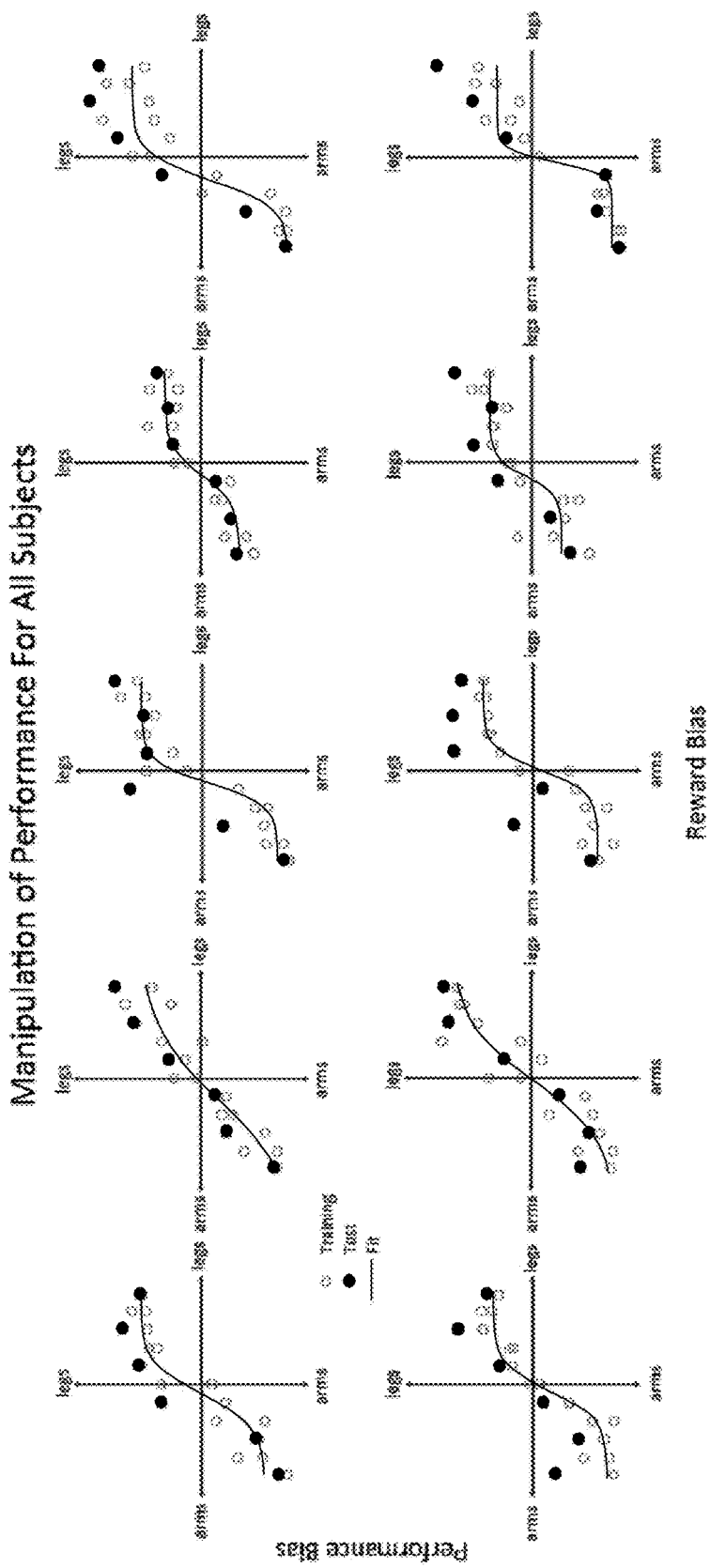
FIG. 9 shows best fit performance bias versus reward bias curves for each individual test subject.

In an independent test of manipulation of performance, 75% of each subject's data was used to train the model of equation (2), while 25% was reserved to test the predictive power of the fit. Each subject's data was chosen such that the training data would span the range of the reward bias. The median R-squared of the fit applied to the test data was found to be $R^2=0.83$. The result indicates the ability to predict future performance based on a relationship fit to an individual subject. The R-squared value for each training set was also determined, and its median value was $R^2=0.90$. This is greater than the R-squared for the population as a whole. This indicates that subject-to-subject discrepancies in preference may exist and/or that each subject adheres more closely to minimizing his or her own subjective effort function than to that of the subject effort function of the population as a whole. FIG. 9 illustrates each individual test subject's performance bias as a function of reward bias.

As noted above, different user's will have different levels of preference for allocating the task between limbs, and this may be due to various factors such as how heavily left or right handed the user is, habit, strength symmetry, etc. The feedback provided by the system may be used to quantify this subjective preference and to determine a subjective cost that the individual will be willing to undertake to change away from that subjective preference. Determination of this information may be obtained based on a user's response to reward bias changes (i.e., the user's response to feedback), or may be determined based on a test sequence designed specifically to determine subjective cost—for example, by testing the user with a neutral (no) bias and then altering the reward bias separately for each input component and measuring the subject's response effort for each limb. Other such methodologies will be apparent to those skilled in the art. This quantified subjective cost may then be recorded and used for profiling of the subject or for later analysis or trending, or may be used for adjusting the reward bias; for example, by making larger reward bias jumps for a user or a particular limb having a high subjective cost.

As one example, determination of subjective cost information may be carried out using a multi-limb exercise machine such as described above. The method may include the steps of:

(a) measuring individual amounts of effort that a subject exerts using two or more limbs against a common resistance;

(b) providing feedback indicating the subject's progress towards a target goal based on a weighted combination of the measured individual amounts of efforts;

(c) altering the weighting of the combination of individual amounts of effort during continued exertion by the subject using the two or more limbs;

(d) providing updated feedback based on the altered weighted combination of measured individual amounts of effort;

(e) obtaining updated measurements of the individual amounts of effort exerted by the subject during step (d); and (f) determining subjective cost information for the subject based on one or more differences between the updated measurements and at least some of the measurements taken before step (d).

This subjective cost information may be represented quantitatively based on the changes in measured effort for each of the different limbs or for combinations of the limbs such as legs together versus arms. By quantitatively knowing the subject cost placed by the user on changing their allocation of effort among various limbs, customized adjustments to the reward bias (weighting) may be provided for each different user, thereby possibly increasing the efficacy of the process and, thus, the rate of progress by the patient or other user.

Some limitations exist regarding the data collection in the above-described experiment. None of these limitations affect the disclosed concepts of subject effort and methods that use a reward bias to take advantage of a subject's tendency to minimize overall subjective effort. These limitations are given below as additional useful guidelines that may require attention when performing or constructing embodiments that are similar to or different than disclosed in the particular experiment above.

It was found that if not explicitly asked to explore the solution space, subjects would sometimes remain at some initial solution, not knowing that the task could be made easier. However, it is believed that if left to perform the task for a long period of time with numerous trials for a number of days, the subjects would eventually discover the lowest subjective effort combinations on their own, without explicit prompting to explore. For purposes of the above experiments, the described familiarization task was used to remove as much of the learning period as possible, thereby accessing information about the subjects' subjective effort more immediately.

It is unknown whether or how much the subjective effort function corresponds to physiological variables such as applied force or metabolic energy expenditure. Other factors such as discomfort, fatigue, or strength discrepancies may ultimately be reflected in the subjective effort function so that energy expenditure is not the sole determining factor. The particular exercise described above did not include continuous movement. The fluctuations in force stemming from reciprocating motion required filtering to provide useable feedback. The filtering introduced some delay in the feedback, which was noticeable and sometimes distracting to some subjects.

It was found that providing a target zone of finite size sometimes altered the strategy of the subject. For example, when a subject would find a combination of arms and legs that would easily satisfy the goal, the feedback would often indicate a work level well beyond the target zone. Instead of using the same combination of effort and slowing down, subjects would sometimes revert to the less effective contribution levels simply because they knew this combination would not surpass the target zone.

There was some subjectivity in the procedure in terms of when to start and stop the collection of data. Another embodiment may include the use of one or more algorithms to determine when a subject's limb efforts have become stable and automatically starting the collection of data.

Finally, the constraint that subjects keep all limbs in contact with the machine, even if they wish to exert little or no work with those limbs, may be a somewhat artificial constraint in view of natural inclinations. However, for purposes of the experiment, it was believed that potential changes in strategy brought about by taking one's limbs off of the machine would confound results across the otherwise continuous spectrum of application of force with all limbs.

One application of the subjective effort framework is neurological rehabilitation. For example, if a patient with weak legs tends to favor his or her arms, a reward bias could be used to incentivize greater leg contributions during rehabilitation. In many tasks, the reason for unequal performance bias may be sensible in terms of the subject's immediate short-term goal of minimizing subjective effort. The reward bias can be used to favor a longer term goal of exercising a weakened limb. Robotic rehabilitation has potential to systematize the incentivizing of exercise for a designated limb.

It is to be understood that the foregoing is a description of one or more embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. For example, although the illustrated embodiments depict a four-limb device having a pair of user-movable components for the arms and a separate pair of user-movable input components for the legs, it will be appreciated that embodiments may only utilize one of these pairs and that other embodiments may utilize equipment that employs less or more input components, such as having only a single pair of user-movable input components (e.g., for the legs only, or for the arms only). All such other embodiments, changes, and modifications are intended to come within the scope of the appended claims.

As used in this specification and claims, the terms "e.g.," "for example," "for instance," and "such as," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. An apparatus, comprising:
a plurality of input components, each of the input components configured to be actuated by different body parts, including a targeted body part, of a user, and each of the input components comprising a surface against which the user exerts effort during actuation;
an input measurement device comprising a transducer associated with each of the input components and configured to measure an amount of energy transferred by the different body parts to each of the input components during actuation;
a processor configured to receive the measurement information from the input measurement devices associated with the input components and apply a reward bias to the received measurement information to determine a contribution from each of the different body parts to a composite performance level,
wherein the reward bias acts such that the contribution from the targeted body part is weighed more than the contribution from another of the different body parts, thereby making the contribution from the targeted body part a disproportionately greater part of the composite performance level than the amount of effort applied by the targeted body part is of the combined efforts applied by each of the different body parts; and
a feedback device in communication with the processor and configured to provide the user with output information indicating the composite performance level relative to a performance target, wherein the composite performance level includes the determined contributions from each of the different body parts actuating the input components.

2. An apparatus as defined in claim 1, wherein the feedback device includes a visual display configured to display to the user the performance target and the composite performance level.

3. An apparatus as defined in claim 2, wherein the contributions from each body part or set of body parts are not shown separately on the visual display.

4. An apparatus as defined in claim 1, wherein the plurality of input components includes two input components coupled together for simultaneous actuation and each of the two input components is configured to be actuated by a different one of the body parts.

5. An apparatus as defined in claim 1, wherein the plurality of input components includes four input components coupled together for simultaneous actuation and each of the four input components is configured to be actuated by a different one of the body parts.

6. An apparatus as defined in claim 1, wherein at least one input measurement device is configured to measure an amount of force applied to the associated input component by the user.

7. An apparatus as defined in claim 1, wherein the plurality of input components includes a right arm input component, a left arm input component, a right leg input component, and a left leg input component and the input components are constructed and arranged to move in a coordinated manner.

8. An apparatus as defined in claim 1, wherein the apparatus is a recumbent stepper for exercising at least some of the user's limbs.

9. An apparatus as defined in claim 1, wherein the feedback device comprises a visual display or a sound generator.

10. A method of increasing function of a targeted body part of a user, the method comprising the steps of:
measuring an amount of effort applied to each of a plurality of different surfaces by the user, wherein the user applies the effort to each of the different surfaces using different body parts, including the targeted body part;
applying a reward bias to the measurements to determine a contribution from each of the different body parts to a composite performance level, wherein the reward bias acts such that the contribution from the targeted body part is weighed more than the contribution from another of the different body parts, thereby making the contribution from the targeted body part a disproportionately greater part of the composite performance level than the amount of effort applied by the targeted body part is of the combined efforts applied by each of the different body parts; and
communicating to the user the composite performance level relative to a performance target, the composite performance level including the determined contributions from each of the different body parts.

11. The method of claim 10, wherein the step of communicating includes visually displaying the composite performance level and the performance target to the user.

12. The method of claim 11, wherein the step of communicating further includes displaying individual contributions from each body part or set of body parts so that the user can observe how the composite performance level changes in relation to additional effort exerted by each body part or set of body parts.

13. The method of claim 11, wherein visually displaying the composite performance level is performed so that individual contributions from each body part or set of body parts are not displayed.

14. An apparatus, comprising:
a pair of user-actuatable input components each comprising a surface against which a user exerts effort during apparatus use, wherein one of the pair of input components is configured to be actuated by a targeted body part of the user exerting effort against the corresponding surface and the other of the pair is configured to be actuated by another body part of the user exerting effort against the corresponding surface, wherein the apparatus is configured to measure the user-exerted efforts and apply a reward bias to the measured efforts to determine a contribution from each of the body parts to a composite performance level that includes the determined contributions from each of the body parts,
wherein the reward bias acts such that the contribution from the targeted body part is weighed more than the contribution from the other body part in the composite performance level, thereby making the contribution from the targeted body part a disproportionately greater part of the composite performance level than the effort exerted by the targeted body part is of the combined efforts exerted by each of the body parts; and
a feedback system that provides a user-discernible feedback when the user exerts more effort with the targeted body part than with the other body part, wherein the user-discernible feedback reduces the overall effort required by the user to meet a performance target, thereby encouraging the exertion of more effort with the targeted body part,
wherein the user-discernible feedback is indicative of the composite performance level relative to the performance target.

15. An apparatus as defined in claim 14, wherein the feedback system provides visual feedback to the user.

16. An apparatus as defined in claim 14, wherein the feedback system provides the user-discernible feedback by adjusting the amount of effort required to actuate at least one of the input components.

* * * * *